(12) United States Patent
Shi et al.

(10) Patent No.: US 8,901,354 B2
(45) Date of Patent: Dec. 2, 2014

(54) METHOD FOR PRODUCING N-SUBSTITUTED AMINE COMPOUNDS THROUGH CATALYZED ALKYLATION

(71) Applicant: Lanzhou Institute of Chemical Physics, Chinese Academy of Sciences, Lanzhou (CN)

(72) Inventors: Feng Shi, Lanzhou (CN); Xinjiang Cui, Lanzhou (CN); Hangkong Yuan, Lanzhou (CN); Youquan Deng, Lanzhou (CN)

(73) Assignee: Lanzhou Institute of Chemical Physics, Chinese Academy of Sciences, Lanzhou (CN)

( * ) Notice: Subject to any disclaimer, the term of this patent is extended or adjusted under 35 U.S.C. 154(b) by 0 days.

(21) Appl. No.: 13/729,664

(22) Filed: Dec. 28, 2012

(65) Prior Publication Data
US 2014/0039181 A1    Feb. 6, 2014

(30) Foreign Application Priority Data

Aug. 1, 2012 (CN) .......................... 2012 1 0271263

(51) Int. Cl.
| | |
|---|---|
| *C07C 209/00* | (2006.01) |
| *C07D 307/52* | (2006.01) |
| *C07D 295/033* | (2006.01) |
| *C07D 213/74* | (2006.01) |
| *C07C 209/68* | (2006.01) |
| *C07C 213/08* | (2006.01) |
| *C07D 217/04* | (2006.01) |
| *C07D 295/03* | (2006.01) |
| *C07D 267/10* | (2006.01) |
| *C07D 213/38* | (2006.01) |
| *C07D 333/20* | (2006.01) |

(52) U.S. Cl.
CPC ............ *C07C 209/68* (2013.01); *C07D 307/52* (2013.01); *C07D 295/033* (2013.01); *C07D 213/74* (2013.01); *C07C 213/08* (2013.01); *C07D 217/04* (2013.01); *C07D 295/03* (2013.01); *C07D 267/10* (2013.01); *C07D 213/38* (2013.01); *C07D 333/20* (2013.01)
USPC ......................................................... 564/395

(58) Field of Classification Search
CPC ..................................................... C07C 209/68
See application file for complete search history.

(56) References Cited

U.S. PATENT DOCUMENTS

| | | |
|---|---|---|
| 3,709,881 A | 1/1973 | Warner |
| 4,268,458 A | 5/1981 | Schulte-Huermann et al. |
| 4,910,304 A | 3/1990 | Fischer et al. |
| 5,068,434 A | 11/1991 | Klug et al. |
| 5,847,131 A | 12/1998 | Simon et al. |
| 5,917,039 A | 6/1999 | Simon et al. |
| 8,071,302 B2 | 12/2011 | Huang |

FOREIGN PATENT DOCUMENTS

| | | |
|---|---|---|
| EP | 0 440 829 A1 | 8/1991 |
| GB | 1 106 084 | 3/1968 |

*Primary Examiner* — Clinton Brooks
(74) *Attorney, Agent, or Firm* — Seed IP Law Group PLLC

(57) ABSTRACT

The invention relates to a method for producing a N-substituted amine compound by catalyzed alkylation. The method uses amine and alcohol or two kinds of amines as the reaction materials, employs composite metal oxides catalyst at a reaction temperature of 80-180° C. to catalyze the reaction for 6-36 hours, so as to produce the N-substituted amine compound. The reaction condition of the method of the invention is relatively moderate, using a catalyst made of cheap non-noble metals, which is non-caustic and easy to be separated and reused. The reaction does not need any medium and has relatively high conversion rate and selectivity.

8 Claims, No Drawings

METHOD FOR PRODUCING N-SUBSTITUTED AMINE COMPOUNDS THROUGH CATALYZED ALKYLATION

FIELD OF THE INVENTION

The invention relates to a method for producing N-substituted amine compounds, specifically, relates to a method for producing N-substituted amine compounds through catalyzed alkylation by using a composite metal oxide catalyst.

BACKGROUND OF THE INVENTION

N-substituted amine compound is a kind of very useful chemical intermediate, which is widely used in the production of dyes, synthetic resins, medicines, and pesticides. It is well known that amine compounds may be produced in large scale in relatively low cost, and the modern industrial production technology of amine compounds has been founded. Therefore, the method for producing N-substituted amine compounds through the coupling reaction between amines and alcohols or the coupling reaction between amines and amines is a route which is very environmental friendly and attracts lots of interests.

Producing N-substituted amine compounds through the alkylation of amines has been researched for several decades, and a serious of catalysts and synthesis methods have been developed. The reaction between diethylene glycol and methylamine has been catalyzed by a precipitated catalyst consisted of CuO/ZnO under the condition of 150-400° C., and 30-400 bar (GB-B-1106084). Another diatomite-supported nickel catalyst shows good catalytic activity for the reaction for producing N-methylmorpholine from diethylene glycol and methylamine under the condition of 225-250° C. and 100 bars, the yield of which achieves 20-60% (U.S. Pat. No. 3,709,881). Patent EP-A-0440829 discloses a precipitated catalyst of cuprum and aluminum which is added with equivalent alkali for the synthesis of N-substituted cyclic amines from glycols and alkyl amines. Another kind of cuprum magnesium silicate, added with 0-2% mass percentage of BaO, $Cr_2O_3$, and ZnO, shows a catalytic activity for the reaction between alkyl amines or dialkyl amines and alcohols at a hydrogen gas pressure of 200 bars to produce N-substituted alkyl amines (U.S. Pat. No. 5,917,039). U.S. Pat. No. 8,071,302 reports an acid zeolite for the reaction between aniline and lower alcohols under the condition of 300-500° C., to selectively produce p-alkyl aniline. U.S. Pat. No. 5,068,434 reports a zeolite with a silicon-aluminum ratio of at least 60 for producing aniline N-alkylation product at 260-330° C. U.S. Pat. No. 5,847,131 reports a Cu catalyst for the N-substitution reaction of alicyclic amines by employing glycols under the condition of 220-280° C. and 100-300 bars, and the catalyst is produced by soaking the $SiO_2$ carrier into an alkali solution with Cu mass percentage of 5-50%. In U.S. Pat. No. 4,268,458, using $POCl_3$ as the catalyst, aniline and aliphatic alcohols or alicyclic alcohols react at 280° C. and a pressure of 60-100 bars to produce 40-90% of N-substituted amine compounds.

Throughout the above various reports, generally, the yield of the product is low, a condition of high temperature and high pressure is generally required, and especially, the problem of the recovery and reuse of the catalyst has not been satisfactorily solved. Therefore, aiming at industrial application, there is strong desire for developing a catalyst for N-substituted amine compounds with high efficiency and ease for recovery and reuse.

SUMMARY OF THE INVENTION

The object of the invention is to provide a method for producing N-substituted amine compounds so as to overcome the disadvantages of the prior art. Specifically, the invention synthesizes the corresponding N-substituted amine compounds under a relatively moderate condition through catalyzed alkylation by using a composite metal oxide catalyst, and thus solves the problems presented in the prior art.

Therefore, in the first aspect, the invention a method for producing N-substituted amine compounds, which uses amine and alcohol or two kinds of amine as the reaction materials, and employs a composite metal oxide catalyst at a reaction temperature of 80-180° C. to catalyze the reaction for 6 to 36 hours, so as to produce N-substituted amine compounds, wherein the amine is selected from an aliphatic amine or an aromatic amine, the alcohol is selected from an aliphatic alcohol or an aromatic alcohol; the composite metal oxide catalyst is selected from CuO—NiO—$Fe_3O_4$, NiO—$Fe_3O_4$, CuO—$Fe_3O_4$ or CuO—NiO.

In a preferred embodiment of the invention, the molar ratio of Cu to Ni is from 10:1 to 1:10, and the molar ratio of Cu to Fe is from 10:1 to 1:10 in CuO—NiO—$Fe_3O_4$.

In a preferred embodiment of the invention, the molar ratio of Ni to Fe in NiO—$Fe_3O_4$ is from 10:1 to 1:10.

In a preferred embodiment of the invention, the molar ratio of Cu to Fe in CuO—$Fe_3O_4$ is from 10:1 to 1:10.

In a preferred embodiment of the invention, the molar ratio of Cu to Ni in CuO—NiO is from 10:1 to 1:10.

In a preferred embodiment of the invention, the structure of the aliphatic amine is selected from:

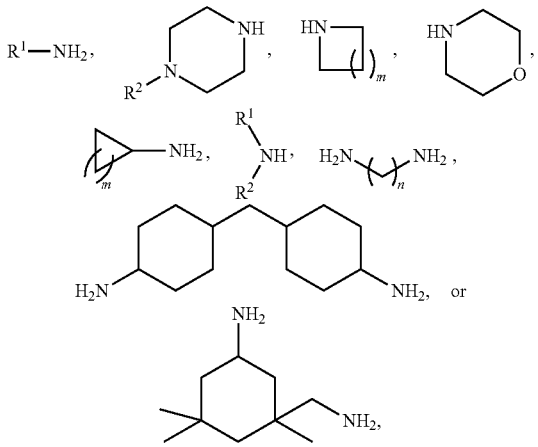

wherein $R^1$ and $R^2$ are each independently selected from any one of a linear or branched alkyl with a carbon number of 1 to 18 and hydrogen, m is an integer of 1 to 6, and n is an integer of 1 to 12;

the structure of the aromatic amine is selected from:

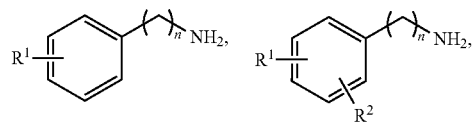

-continued

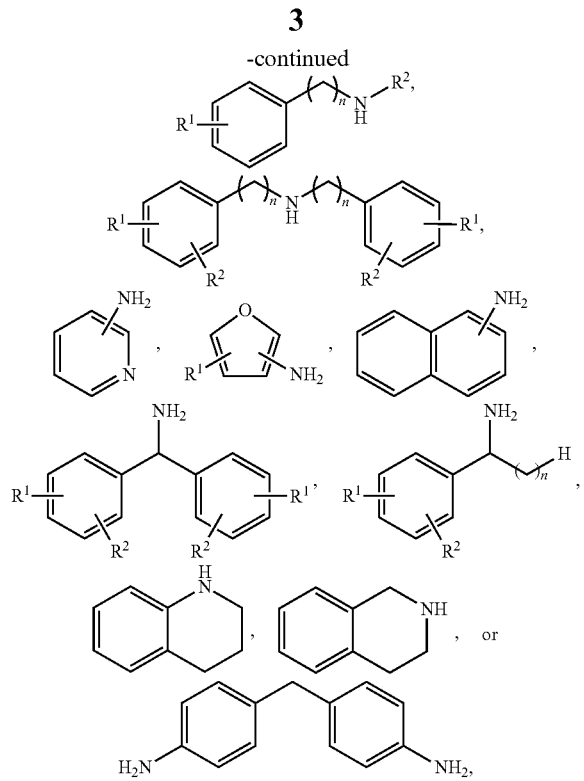

wherein $R^1$ and $R^2$ are each independently selected from any one of a linear or branched alkyl with a carbon number of 1 to 18, hydrogen, methoxyl, phenyl, phenoxy, fluorine, chlorine, bromine, and iodine, n is an integer of 0 to 12;

the structure of the aliphatic alcohol is selected from:

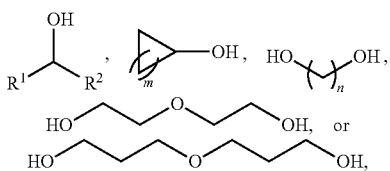

wherein $R^1$ and $R^2$ are each independently selected from any one of a linear or branched alkyl with a carbon number of 1 to 18 and hydrogen, m is an integer of 1 to 6, and n is an integer of 2 to 8;

the structure of the aromatic alcohol is selected from:

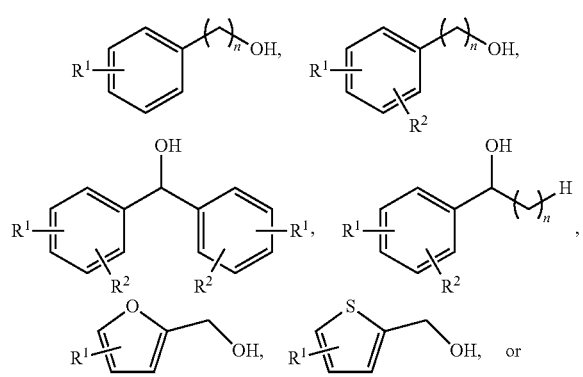

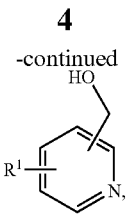

wherein $R^1$ and $R^2$ are each independently selected from any one of a linear or branched alkyl with a carbon number of 1 to 18, hydrogen, methoxyl, phenyl, phenoxy, fluorine, chlorine, bromine, and iodine, n is an integer of 1 to 4.

In another preferred embodiment of the invention, the mass ratio between the composite metal oxide catalyst and the amine is from 0.01:1 to 1.2:1.

In the second aspect, the invention provides a method for producing the composite metal oxide catalyst, comprising the following steps:

1) adding an aqueous solution of any two or three ones selected from $Cu(NO_3)_2$, $Ni(NO_3)_2$, and $Fe(NO_3)_3$, and an aqueous $Al(NO_3)_3$ solution, to aqueous alkali metal oxide or hydroxide solution, aqueous ammonia, or aqueous carbamide solution which functions as a precipitator (preferably an aqueous solution of NaOH, $Na_2CO_3$, KOH, $K_2CO_3$, $NH_3$, or carbamide) to coprecipitate, followed by washing, drying in the air, calcining, and reducing in hydrogen gas, thereby obtaining a crude catalyst;

2) using an aqueous alkali metal hydroxide solution (preferably NaOH or KOH) to remove the alumina in the crude catalyst obtained in step 1), producing a composite metal oxides catalyst CuO—NiO—$Fe_3O_4$, NiO—$Fe_3O_4$, CuO—$Fe_3O_4$, or CuO—NiO.

In a preferred embodiment of the catalyst production method of the invention, the coprecipitation is conducted at room temperature with a coprecipitation duration of 1 to 4 hours; the drying temperature of the catalyst may be 50-180° C., the calcining temperature may be 300-800° C., and the reducing temperature may be 300-800° C.

In the third aspect, the invention provides composite metal oxide catalyst CuO—NiO—$Fe_3O_4$, NiO—$Fe_3O_4$, CuO—$Fe_3O_4$, or CuO—NiO produced by the catalyst production method of the invention, wherein the molar ratio of Cu to Ni in CuO—NiO—$Fe_3O_4$ is from 10:1 to 1:10, the molar ratio of Cu to Fe is from 10:1 to 1:10; the molar ratio of Ni to Fe in NiO—$Fe_3O_4$ is from 10:1 to 1:10; the molar ratio of Cu to Fe in CuO—$Fe_3O_4$ is from 10:1 to 1:10; and the molar ratio of Cu to Ni in CuO—NiO is from 10:1 to 1:10.

Comparing with the traditional process, the invention has the following advantages.

1. The composite metal oxide catalyst employed by the invention possesses the advantages of high activity, high yield, and is reusable.

2. The catalyst production method of the invention is simple, all of the components used are cheap non-noble metals, providing very high cost effectiveness ratio.

3. The reaction condition of the method of the invention is relatively moderate, and a catalyst used in the method of the invention is non-caustic and easy to be separated and reused.

4. The reaction does not need any medium and has relatively high conversion rate and selectivity.

DETAILED DESCRIPTION OF THE INVENTION

Definition

N-substituted amine compound: in the present invention, N-substituted amine compound refers to N-substituted primary amine, N,N-disubstituted secondary amine or N,N,N-trisubstituted tertiary amine, the amine compound is preferably a linear or branched alkyl amine with a carbon number of 1 to 18 or a linear or branched aromatic amine having an aromatic ring substituent with a carbon number of 1 to 18.

Composite metal oxide catalyst: in the present invention, composite metal oxide catalyst refers to a catalyst which is produced by compounding two or three kinds of metal oxides by a certain method. In the invention it specifically refers to the catalyst produced by compounding cupric oxide, nickel oxide, and ferric oxide.

The invention relates to a method for producing a N-substituted amine compound, which uses amine and alcohol or two kinds of amine as the reaction materials, and employs a composite metal oxide catalyst at a reaction temperature of 80-180° C. to catalyze the reaction for 6 to 36 hours, so as to produce the N-substituted amine compound, wherein the amine is selected from an aliphatic amine with a carbon atom number of 1 to 18 or an aromatic amine having an aromatic cyclic substituent with a carbon atom number of 1 to 18, the alcohol is selected from an aliphatic alcohol with a carbon atom number of 1 to 18 or an aromatic amine having an aromatic cyclic substituent with a carbon atom number of 1 to 18; the composite metal oxide catalyst is selected from $CuO$—$NiO$—$Fe_3O_4$, $NiO$—$Fe_3O_4$, $CuO$—$Fe_3O_4$ or $CuO$—$NiO$.

Moreover, the invention relates to a method for producing the composite metal oxide catalyst of the invention, the method comprises the following steps:

1) adding an aqueous solution of any two or three ones selected from $Cu(NO_3)_2$, $Ni(NO_3)_2$, and $Fe(NO_3)_3$ according to the ratio of Cu, Ni, and Fe in the finial catalyst product, and an aqueous $Al(NO_3)_3$ solution with a Al molar ratio of 15% with respect to the total content of Cu, Ni, and Fe components, to aqueous alkali metal oxide or hydroxide solution, aqueous ammonia, or aqueous carbamide solution which functions as a precipitator to coprecipitate, followed by washing, drying in the air, calcining, and reducing in hydrogen gas, thereby obtaining a crude catalyst;

2) using an aqueous alkali metal hydroxide solution to remove the alumina in the crude catalyst obtained in step 1), producing a composite metal oxides catalyst $CuO$—$NiO$—$Fe_3O_4$, $NiO$—$Fe_3O_4$, $CuO$—$Fe_3O_4$, or $CuO$—$NiO$, respectively.

The catalysts obtained in the above method relates to Ni, Cu, and Fe catalysts which are potentially active to the applied reaction. As for the alkylation reaction between amines and alcohols, all of Ni, Cu, and Fe have certain catalytic activity. However, according to the experience and the finished research findings of the inventor, Ni and Fe catalysts have better performance in the step of generating N-substituted amine, but Cu catalyst has better performance in the step of the activation of alcohol. By combining them, it is possible to obtain better catalyst system for the alkylation reaction between amines and alcohols, so as to achieve the production of N-substituted amine compounds under a relatively moderate condition. Meanwhile, in the above catalysts, it is preferred to formulate such catalyst according to the preferred molar ratio between each oxides disclosed by the invention. If the content of one component is lower than the ratio described in the present Description, it will significantly lower the activity of the finished catalyst. During the production of the catalyst, the addition of aluminium nitrate is the key operation for obtaining catalysts with high activity. More catalytic active sites may be formed by removing aluminum.

Although the composite metal oxide catalyst of the invention could not be directly obtained from the market and are necessarily to be produced according to the method described in the Description of the present invention, it is very easy for a person skilled in the art to produce it in view of the teaching of the present invention.

The invention is further described below by way of the Examples. The Examples are only used to illustrate the implementation and the effects of the invention, and is not intended to limit the scope of the invention in any manner.

EXAMPLE 1

Cupric nitrate trihydrate 1.25 g, nickel nitrate hexahydrate 6.0 g, ferric nitrate nonahydrate 2.0 g, and aluminum nitrate nonahydrate 2.0 g were weighted and added to 150 mL of water. After the dissolution was completed, 50 mL of 1.7 mol/L aqueous $Na_2CO_3$ solution was dropwise added under stirring, followed by stirred at room temperature for 2 h. The resultant was centrifuged, washed to neutrality, dried at 120° C. for 4 hours, calcined at 450° C. for 4 hours, reduced under hydrogen gas atmosphere at 450° C. for 2 h, and then treated with 10 mol/L aqueous NaOH solution to remove aluminium. The obtained catalyst was sequentially washed with ethanol and ether, and further dried in the air to obtain $CuO$—$NiO$—$Fe_3O_4$ catalyst black powder (catalyst A).

EXAMPLE 2

Nickel nitrate hexahydrate 6.0 g, ferric nitrate nonahydrate 2.0 g, and aluminum nitrate nonahydrate 2.0 g were weighted and added to 150 mL of water. After the dissolution was completed, 50 mL of 1.7 mol/L aqueous $Na_2CO_3$ solution was dropwise added under stirring, followed by stirred at room temperature for 2 h. The resultant was centrifuged, washed to neutrality, dried at 120° C. for 4 hours, calcined at 450° C. for 4 hours, reduced under hydrogen gas atmosphere at 450° C. for 2 h, and then treated with 10 mol/L aqueous NaOH solution to remove aluminium. The obtained catalyst was sequentially washed with ethanol and ether, and dried in the air to obtain $NiO$—$Fe_3O_4$ catalyst black powder (catalyst B).

EXAMPLE 3

Cupric nitrate trihydrate 1.25 g, ferric nitrate nonahydrate 2.0 g, and aluminum nitrate nonahydrate 2.0 g were weighted and added to 150 mL of water. After the dissolution was completed, 50 mL of 1.7 mol/L aqueous $Na_2CO_3$ solution was dropwise added under stirring, followed by stirred at room temperature for 2 h. The resultant was centrifuged, washed to neutrality, dried at 120° C. for 4 hours, calcined at 450° C. for 4 hours, reduced under hydrogen gas atmosphere at 450° C. for 2 h, and then treated with 10 mol/L aqueous NaOH solution to remove aluminium. The obtained catalyst was sequentially washed with ethanol and ether, and dried in the air to obtain $CuO$—$Fe_3O_4$ catalyst black powder (catalyst C).

EXAMPLE 4

Cupric nitrate trihydrate 1.25 g, nickel nitrate hexahydrate 6.0 g, and aluminum nitrate nonahydrate 2.0 g were weighted and added to 150 mL of water. After the dissolution was completed, 50 mL of 1.7 mol/L aqueous $Na_2CO_3$ solution was dropwise added under stirring, followed by stirred at room temperature for 2 h. The resultant was centrifuged, washed to neutrality, dried at 120° C. for 4 hours, calcined at 450° C. for 4 hours, reduced under hydrogen gas atmosphere at 450° C. for 2 h, and then treated with 10 mol/L aqueous NaOH solution to remove aluminium. The obtained catalyst was sequentially washed with ethanol and ether, and dried in the air to obtain CuO—NiO catalyst black powder (catalyst D).

EXAMPLE 5

Cupric nitrate trihydrate 1.25 g, nickel nitrate hexahydrate 6.0 g, and aluminum nitrate nonahydrate 2.0 g were weighted and added to 150 mL of water. After the dissolution was completed, 50 mL of 1.7 mol/L aqueous $K_2CO_3$ solution was dropwise added under stirring, followed by stirred at room temperature for 2 h. The resultant was centrifuged, washed to neutrality, dried at 50° C. for 8 hours, calcined at 300° C. for 8 hours, reduced under hydrogen gas atmosphere at 800° C. for 1 h, and then treated with 10 mol/L aqueous KOH solution to remove aluminium. The obtained catalyst was sequentially washed with ethanol and ether, and dried in the air to obtain CuO—NiO catalyst black powder (catalyst E).

EXAMPLE 6

Cupric nitrate trihydrate 1.25 g, nickel nitrate hexahydrate 6.0 g, and aluminum nitrate nonahydrate 2.0 g were weighted and added to 150 mL of water. After the dissolution was completed, 50 mL of 25 wt % aqueous ammonia solution was dropwise added under stirring, followed by stirred at room temperature for 2 h. The resultant was centrifuged, washed to neutrality, dried at 180° C. for 2 hours, calcined at 600° C. for 3 hours, reduced under hydrogen gas atmosphere at 300° C. for 6 h, and then treated with 10 mol/L aqueous NaOH solution to remove aluminium. The obtained catalyst was sequentially washed with ethanol and ether, and dried in the air to obtain CuO—NiO catalyst black powder (catalyst F).

EXAMPLE 7

Cupric nitrate trihydrate 1.25 g, nickel nitrate hexahydrate 6.0 g, and aluminum nitrate nonahydrate 2.0 g were weighted and added to 150 mL of water. After the dissolution was completed, 50 mL of 2 mol/L aqueous carbamide solution was dropwise added under stirring, followed by stirred at room temperature for 2 h. The resultant was centrifuged, washed to neutrality, dried at 120° C. for 4 hours, calcined at 800° C. for 2 hours, reduced under hydrogen gas atmosphere at 450° C. for 2 h, and then treated with 10 mol/L aqueous NaOH solution to remove aluminium. The obtained catalyst was sequentially washed with ethanol and ether, and dried in the air to obtain CuO—NiO catalyst black powder (catalyst G).

EXAMPLE 8

Cupric nitrate trihydrate 1.25 g, nickel nitrate hexahydrate 6.0 g, and aluminum nitrate nonahydrate 2.0 g were weighted and added to 150 mL of water. After the dissolution was completed, 50 mL of 2 mol/L NaOH solution was dropwise added under stirring, followed by stirred at room temperature for 2 h. The resultant was centrifuged, washed to neutrality, dried at 140° C. for 4 hours, calcined at 400° C. for 4 hours, reduced under hydrogen gas atmosphere at 500° C. for 2 h, and then treated with 10 mol/L aqueous NaOH solution to remove aluminium. The obtained catalyst was sequentially washed with ethanol and ether, and dried in the air to obtain CuO—NiO catalyst black powder (catalyst H).

EXAMPLES 9-16

90 mg of Each of catalysts A, B, C, D, E, F, G, and H obtained in Examples 1-8, as well as 0.5 mmol (0.465 g) aniline and 0.5 mmol (0.540 g) benzyl alcohol for each catalyst, were respectively added into a 40 mL glass reaction tube provided with a magnetic stirring apparatus in turn. After sealed, the tube was purged with $N_2$ to replace the air in the system for three times. Next, the system was heated and stirred. The temperature was raised to 150° C. and then kept at that temperature for 20 hours. The reaction was then stopped and the system was cooled down to the room temperature. The catalyst was obtained from the reaction mixture by filtration. Agilent 7890A (30 m×0.25 mm×0.33 μm capillary column, hydrogen flame ionization detector) gas chromatograph was used for quantitatively analyzing the reaction mixture. The other byproducts were qualitatively analyzed with Agilent 6890/5973 Gas Chromatography-Mass Spectrometer (equipped with NIST Mass Spectral Database chemical workstation, 30 m×0.25 mm×0.33 μm capillary column). The reaction product is N-benzylaniline, and the analysis result is shown in Table 1.

TABLE 1

| Example | Catalyst | Yield(%) |
|---------|----------|----------|
| 9  | A | 91 |
| 10 | B | 55 |
| 11 | C | 62 |
| 12 | D | 93 |
| 13 | E | 84 |
| 14 | F | 79 |
| 15 | G | 90 |
| 16 | H | 87 |

EXAMPLE 17

The catalyst D obtained in Example 8 was centrifuged, washed, dried, and then, added into a 40 mL glass reaction tube provided with a magnetic stirring apparatus together with 5 mmol (0.465 g) aniline and 5 mmol (0.540 g) benzyl alcohol. After sealed, the tube was purged with $N_2$ to replace the air in the system for three times. Next, the system was heated and stirred. The test of the reuse performance was conducted. The temperature was raised to 150° C. and then kept at that temperature for 20 hours. The separation and reuse of the catalyst was repeated for four times, that is, conducting the second, third, fourth, and fifth service performance research. After the reaction, Agilent 7890A (30 m×0.25 mm×0.33 μm capillary column, hydrogen flame ionization detector) gas chromatograph was used for quantitatively analyzing the reaction mixture. The other byproducts were qualitatively analyzed with Agilent 6890/5973 Gas Chromatography-Mass Spectrometer (equipped with NIST Mass Spectral Database chemical workstation, 30 m×0.25 mm×0.33 μm capillary column). The yields of N-benzylaniline were 90%, 88%, 88%, and 87%, respectively.

EXAMPLES 18-63

With reference to the conditions used in Examples 9-16, 60-150 mg of catalyst D obtained in Example 4 was weighted and added into a 40 mL glass reaction tube provided with a magnetic stirring apparatus containing 5 mmol amines having different structures and 5 mmol alcohols having different structures, respectively. After sealed, the tube was purged with $N_2$ to replace the air in the system for three times. Next, the system was heated and stirred. The temperature was raised to 80-180° C. and then kept for 6-36 hours. The reaction was then stopped and the system was cooled down to the room temperature. The catalyst was obtained from the reaction mixture by filtration. Agilent 7890A (30 m×0.25 mm×0.33 μm capillary column, hydrogen flame ionization detector) gas chromatograph was used for quantitatively analyzing the reaction mixture. The other byproducts were qualitatively analyzed with Agilent 6890/5973 Gas Chromatography-Mass Spectrometer (equipped with NIST Mass Spectral Database chemical workstation, 30 m×0.25 mm×0.33 μm capillary column). Each of the analysis results was shown in Table 2.

TABLE 2

| Example | Catalyst/ mg | Temperature/ ° C. | Time/ h | Reactant 1 | Reactant 2 |
| --- | --- | --- | --- | --- | --- |
| 18 | 60 | 150 | 20 | aniline | benzyl alcohol |
| 19 | 60 | 160 | 16 | 4-methylaniline | benzyl alcohol |
| 20 | 60 | 160 | 18 | 4-methoxyaniline | benzyl alcohol |
| 21 | 80 | 160 | 20 | 4-chloroaniline | benzyl alcohol |
| 22 | 80 | 160 | 24 | 4-bromoaniline | benzyl alcohol |
| 23 | 80 | 160 | 20 | 2-aminopyridine | benzyl alcohol |
| 24 | 100 | 140 | 12 | 1-naphthylamine | benzyl alcohol |
| 25 | 100 | 160 | 18 | 1-phenylethylamine | benzyl alcohol |
| 26 | 100 | 140 | 20 | 3-aminobiphenyl | benzyl alcohol |
| 27 | 110 | 140 | 15 | cyclohexylamine | benzyl alcohol |

TABLE 2-continued
| | | | | | |
|---|---|---|---|---|---|
| 28 | 110 | 150 | 10 | 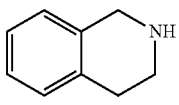 | 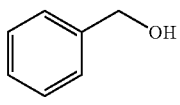 |
| 29 | 110 | 150 | 18 | 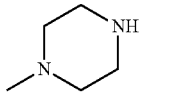 | 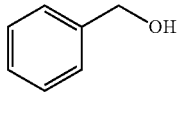 |
| 30 | 110 | 150 | 16 | 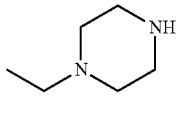 | 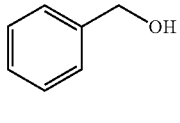 |
| 31 | 110 | 145 | 18 | 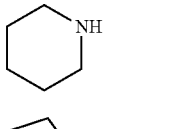 | 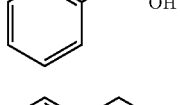 |
| 32 | 110 | 150 | 9 | 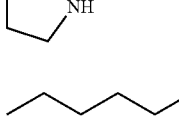 | 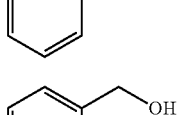 |
| 33 | 110 | 120 | 8 | 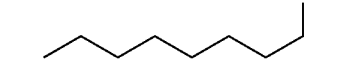 | 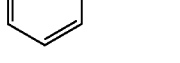 |
| 34 | 130 | 110 | 18 | 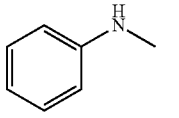 | 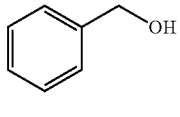 |
| 35 | 100 | 120 | 15 | 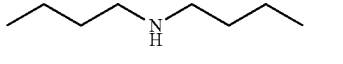 | 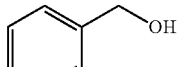 |
| 36 | 130 | 150 | 20 | 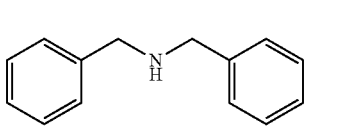 [SMILES: c1ccc(CNCc2ccccc2)cc1] | 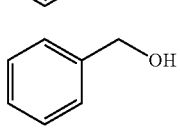 |
| 37 | 60 | 110 | 36 | 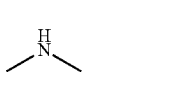 | 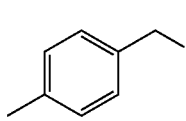 |
| 38 | 60 | 140 | 24 | 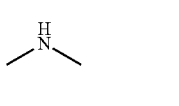 | 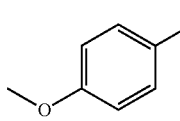 |
| 39 | 60 | 140 | 20 | 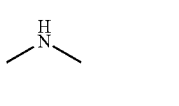 | 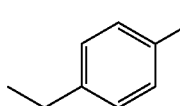 |
| 40 | 80 | 150 | 18 | 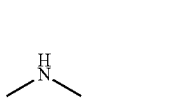 | 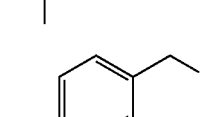 |
| 41 | 100 | 150 | 12 | 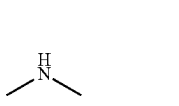 | 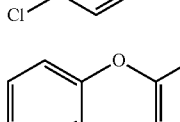 |

TABLE 2-continued

| # | | | | Amine | Alcohol |
|---|---|---|---|---|---|
| 42 | 80 | 180 | 6 | dimethylamine (CH3-NH-CH3) | 2-phenylethanol (PhCH2CH2OH) |
| 43 | 80 | 180 | 6 | dimethylamine | C7H15-CH2OH |
| 44 | 80 | 180 | 8 | dimethylamine | C11H23-CH2OH |
| 45 | 80 | 160 | 15 | dimethylamine | thiophene-2-methanol |
| 46 | 150 | 160 | 10 | 4,4'-methylenedianiline (H2N-C6H4-CH2-C6H4-NH2) | 1,4-butanediol (HO-(CH2)4-OH) |
| 47 | 135 | 150 | 20 | 2,4-dimethylaniline | 1,4-butanediol |
| 48 | 135 | 150 | 20 | 2,6-dimethylaniline | 1,4-butanediol |
| 49 | 80 | 150 | 16 | cyclohexylamine | 1,4-butanediol |
| 50 | 100 | 140 | 24 | C7H15-CH2-NH2 | 1,4-butanediol |
| 51 | 100 | 140 | 24 | 1,6-hexanediamine (H2N-(CH2)6-NH2) | 1,4-butanediol |
| 52 | 100 | 150 | 16 | p-toluidine | 1,6-hexanediol |
| 53 | 100 | 150 | 18 | p-toluidine | diethylene glycol (HO-CH2CH2-O-CH2CH2-OH) |
| 54 | 100 | 150 | 20 | p-toluidine | HO-CH2CH2-O-CH2CH2CH2-OH |
| 55 | 130 | 150 | 20 | n-butylamine | 1-phenylethanol |
| 56 | 80 | 145 | 12 | n-butylamine | isopropanol |

TABLE 2-continued

| # | | | | Amine | Alcohol |
|---|---|---|---|---|---|
| 57 | 80 | 160 | 14 | N-methylaniline (PhNH-CH₃) | cyclohexanol |
| 58 | 100 | 140 | 18 | N-methylbenzylamine (PhCH₂-NH-CH₃) | cyclohexanol |
| 59 | 130 | 130 | 24 | aniline (PhNH₂) | furfuryl alcohol |
| 60 | 130 | 130 | 24 | aniline (PhNH₂) | 2-pyridylmethanol |
| 61 | 100 | 160 | 20 | NH₃ | furfuryl alcohol |
| 62 | 80 | 180 | 24 | NH₃ | 2-pentanol |
| 63 | 80 | 140 | 24 | NH₃ | 2-butanol |

| Example | Product | Yield/% |
|---|---|---|
| 18 | N-benzylaniline (Ph-NH-CH₂-Ph) | 93 |
| 19 | N-benzyl-4-methylaniline (4-Me-C₆H₄-NH-CH₂-Ph) | 89 |
| 20 | N-benzyl-4-methoxyaniline (4-MeO-C₆H₄-NH-CH₂-Ph) | 85 |
| 21 | N-benzyl-4-chloroaniline (4-Cl-C₆H₄-NH-CH₂-Ph) | 87 |

TABLE 2-continued
| | | |
|---|---|---|
| 22 | 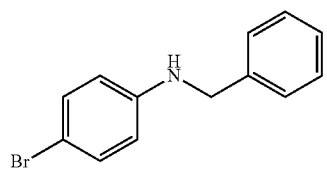 [SMILES: Brc1ccc(NCc2ccccc2)cc1] | 79 |
| 23 | 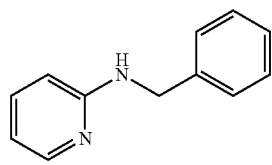 [SMILES: c1ccc(CNc2ccccn2)cc1] | 81 |
| 24 | 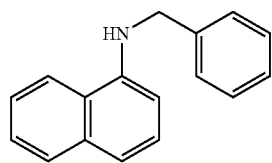 [SMILES: c1ccc(CNc2cccc3ccccc23)cc1] | 75 |
| 25 | 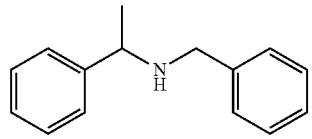 [SMILES: CC(NCc1ccccc1)c1ccccc1] | 86 |
| 26 | 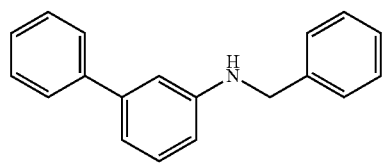 [SMILES: c1ccc(CNc2cccc(-c3ccccc3)c2)cc1] | 83 |
| 27 | 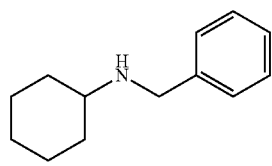 [SMILES: c1ccc(CNC2CCCCC2)cc1] | 86 |
| 28 | 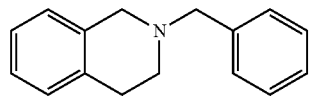 [SMILES: c1ccc(CN2CCc3ccccc3C2)cc1] | 86 |
| 29 | 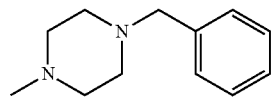 | 81 |
| 30 | 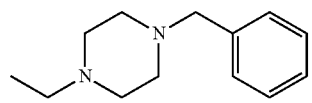 | 76 |
| 31 | 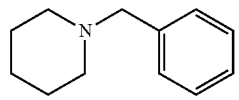 [SMILES: c1ccc(CN2CCCCC2)cc1] | 83 |
| 32 | 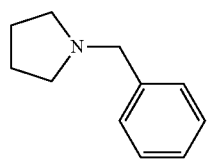 [SMILES: c1ccc(CN2CCCC2)cc1] | 71 |

TABLE 2-continued

| | | |
|---|---|---|
| 33 | CH₃(CH₂)₇N(CH₂C₆H₅)(CH₂)₇CH₃ (dioctyl benzyl amine) | 65 |
| 34 | N-methyl-N-benzylaniline | 70 |
| 35 | N,N-dibutylbenzylamine | 80 |
| 36 | tribenzylamine | 75 |
| 37 | N,N-dimethyl-4-methylbenzylamine | 76 |
| 38 | N,N-dimethyl-4-methoxybenzylamine | 80 |
| 39 | N,N-dimethyl-4-isopropylbenzylamine | 81 |
| 40 | N,N-dimethyl-4-chlorobenzylamine | 73 |

TABLE 2-continued
| | | |
|---|---|---|
| 41 | 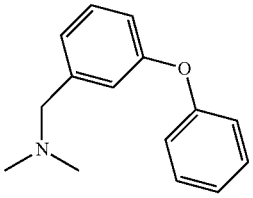 [SMILES: CN(C)Cc1cccc(Oc2ccccc2)c1] | 69 |
| 42 | 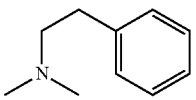 | 75 |
| 43 | 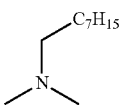 | 80 |
| 44 | 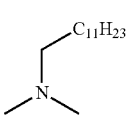 | 89 |
| 45 | 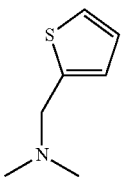 | 81 |
| 46 | 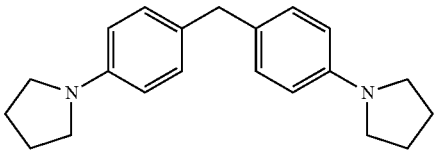 [SMILES: c1cc(N2CCCC2)ccc1Cc1ccc(N2CCCC2)cc1] | 64 |
| 47 | 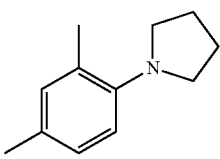 | 90 |
| 48 | 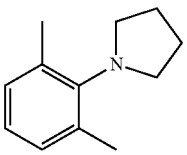 | 89 |
| 49 | 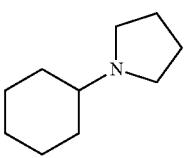 [SMILES: C1CCC(N2CCCC2)CC1] | 90 |
| 50 | 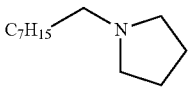 | 91 |

TABLE 2-continued
| | | |
|---|---|---|
| 51 | 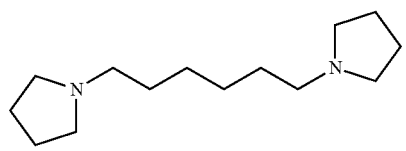 [SMILES: C(CCCN1CCCC1)CCN1CCCC1] | 67 |
| 52 | 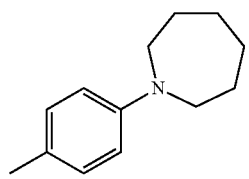 | 86 |
| 53 | 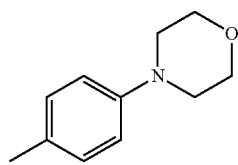 | 81 |
| 54 | 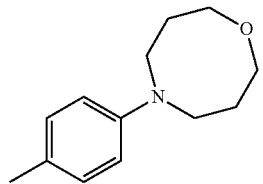 | 83 |
| 55 | 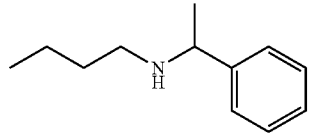 | 86 |
| 56 | 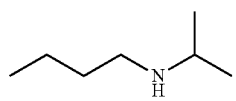 | 67 |
| 57 | 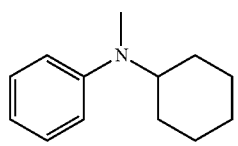 | 75 |
| 58 | 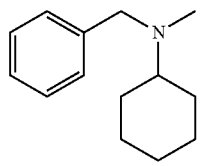 | 81 |
| 59 | 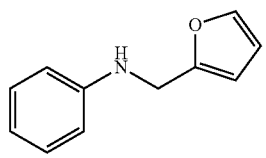 [SMILES: c1ccc(NCc2ccco2)cc1] | 86 |
| 60 | 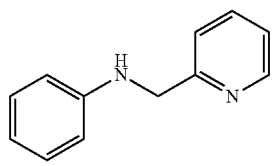 [SMILES: c1ccc(NCc2ccccn2)cc1] | 75 |

TABLE 2-continued

| | | | |
|---|---|---|---|
| 61 | furfuryl-NH-furfuryl (di(furan-2-ylmethyl)amine) | | 36 |
| 62 | di(pentan-2-yl)amine branched structure | | 95 |
| 63 | di(sec-butyl)amine / di(butan-2-yl)amine | | 68 |

EXAMPLES 64-67

With reference to the conditions used in Examples 5-8, 100 mg of catalyst D obtained in Example 4 and 5 mmol alcohols were weighted and added into a 90 mL glass reaction tube provided with a magnetic stirring apparatus. After sealed, the tube was purged with $N_2$ to replace the air in the system for three times. Next, 50 mmol ammonia gas was charged. The temperature was raised to 160° C. and then kept at that temperature for 24 hours. The reaction was then stopped and the system was cooled down to the room temperature. The catalyst was obtained from the reaction mixture by filtration. Agilent 7890A (30 m×0.25 mm×0.33 μm capillary column, hydrogen flame ionization detector) gas chromatograph was used for quantitatively analyzing the reaction mixture. The other byproducts were qualitatively analyzed with Agilent 6890/5973 Gas Chromatography-Mass Spectrometer (equipped with NIST Mass Spectral Database chemical workstation, 30 m×0.25 mm×0.33 μm capillary column). Each of the analysis results was shown in Table 3. The N-substituted amines produced at this time were primary amines.

EXAMPLES 68-75

With reference to the conditions in Examples 5-8, 80-150 mg of catalyst D obtained in Example 4 and 10 mmol of amines having different structures were weighted and added into a 40 mL glass reaction tube provided with a magnetic stirring apparatus. After sealed, the tube was purged with $N_2$ to replace the air in the system for three times. Next, the system was heated and stirred. The temperature was raised to 150-170° C. and then kept for 18-24 hours. The reaction was then stopped and the system was cooled down to the room temperature. The catalyst was obtained from the reaction mixture by filtration. Agilent 7890A (30 m×0.25 mm×0.33 μm capillary column, hydrogen flame ionization detector) gas chromatograph was used for quantitatively analyzing the reaction mixture. The other byproducts were qualitatively analyzed with Agilent 6890/5973 Gas Chromatography-Mass Spectrometer (equipped with NIST Mass Spectral Database chemical workstation, 30 m×0.25 mm×0.33 μm capillary column). The reaction products were secondary amines. Each of the analysis results was shown in Table 4.

TABLE 3

| Example | Amine | alcohol | Product | The chromatographic yield of N-substituted amine/% |
|---|---|---|---|---|
| 64 | $NH_3$ | benzyl alcohol (PhCH₂OH) | benzylamine (PhCH₂NH₂) | 75 |
| 65 | $NH_3$ | 4-chlorobenzyl alcohol | 4-chlorobenzylamine | 40 |
| 66 | $NH_3$ | pyridin-2-ylmethanol | pyridin-2-ylmethanamine | 58 |
| 67 | $NH_3$ | $C_{11}H_{23}$-CH₂OH | $C_{11}H_{23}$-CH₂NH₂ | 55 |

TABLE 4

| Example | Catalyst/ mg | Temperature/ °C. | Time/ h | Reactant | Product | The chromatographic yield of N-substituted amine/% |
|---|---|---|---|---|---|---|
| 68 | 100 | 150 | 24 | benzylamine | dibenzylamine | 81 |
| 69 | 150 | 150 | 20 | 4-chlorobenzylamine | bis(4-chlorobenzyl)amine | 58 |
| 70 | 80 | 150 | 24 | 4-methylbenzylamine | bis(4-methylbenzyl)amine | 88 |
| 71 | 100 | 150 | 20 | 4-methoxybenzylamine | bis(4-methoxybenzyl)amine | 83 |
| 72 | 150 | 170 | 20 | 1-phenylethylamine | bis(1-phenylethyl)amine | 61 |
| 73 | 80 | 150 | 18 | cyclohexylamine | dicyclohexylamine | 91 |
| 74 | 150 | 150 | 24 | $C_{11}H_{23}CH_2NH_2$ | $(C_{11}H_{23}CH_2)_2NH$ | 75 |
| 75 | 150 | 130 | 20 | butylamine | dibutylamine | 60 |

The invention claimed is:

1. A method for producing a N-substituted amine compound, comprising:
reacting a first amine with an alcohol or with a second amine in the presence of a composite metal oxide catalyst,
wherein the composite metal oxides catalyst is CuO—NiO—$Fe_3O_4$, NiO—$Fe_3O_4$, CuO—$Fe_3O_4$ or CuO—NiO;
wherein the first amine and the second amine are the same or different and independently
(1) an aliphatic amine selected from group consisting of

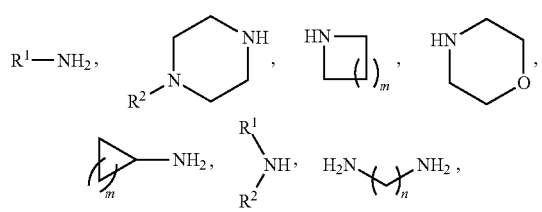

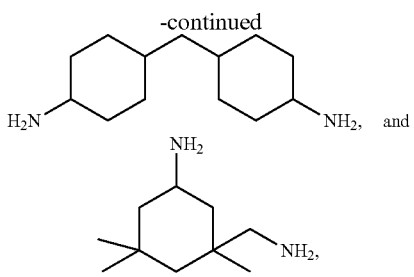

wherein $R^1$ and $R^2$ are each independently a linear or branched alkyl with a carbon number of 1 to 18 or hydrogen, m is an integer of 1 to 6, and n is an integer of 1 to 12; or (2) an aromatic amine selected from group consisting of

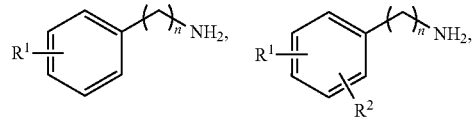

-continued

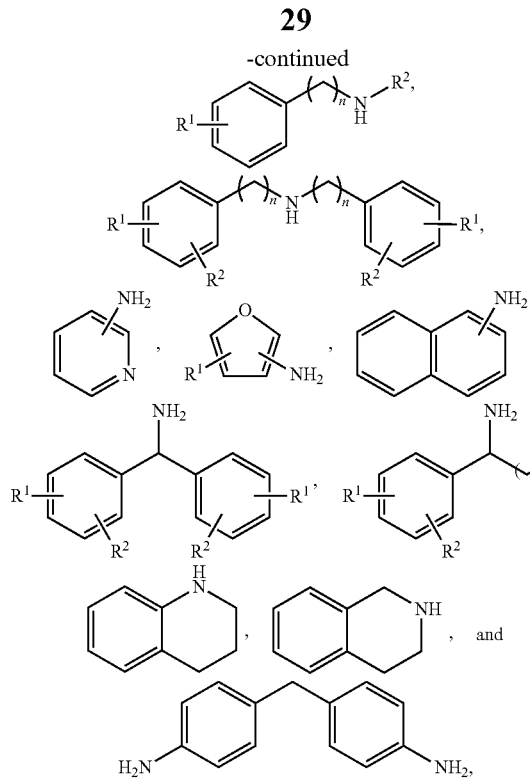

wherein R[1] and R[2] are each independently a linear or branched alkyl with a carbon number of 1 to 18, hydrogen, methoxyl, phenyl, phenoxyl, fluorine, chlorine, bromine, or iodine, n is an integer of 0 to 12;

wherein the alcohol is (1) an aliphatic alcohol selected from the group consisting of:

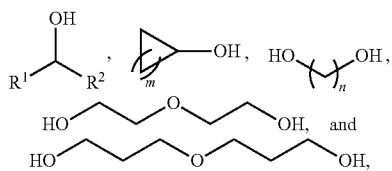

wherein R[1] and R[2] are each independently a linear or branched alkyl with a carbon number of 1 to 18 or a hydrogen, m is an integer of 1 to 6, and n is an integer of 2 to 8; or (2) an aromatic alcohol selected from the group consisting of:

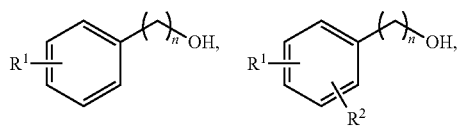

-continued

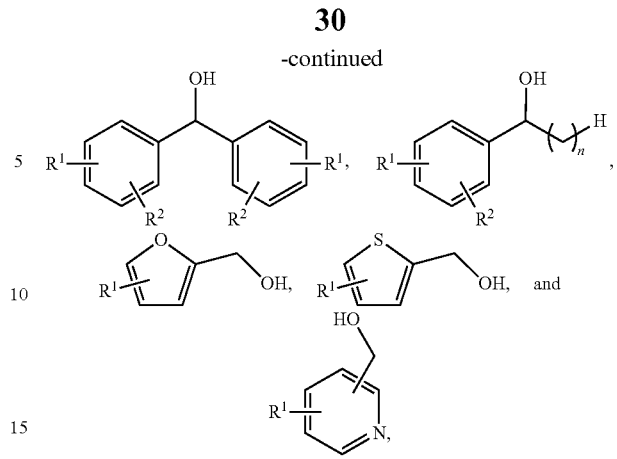

wherein R[1] and R[2] are each independently a linear or branched alkyl with a carbon number of 1 to 18, hydrogen, methoxyl, phenyl, phenoxy, fluorine, chlorine, bromine, or iodine, n is an integer of 1 to 4; and wherein the composite metal oxide catalyst is produced by the following steps:

1) adding an aqueous solution of any two or three nitrates selected from $Cu(NO_3)_2$, $Ni(NO_3)_2$, and $Fe(NO_3)_3$, and an aqueous $Al(NO_3)_3$ solution, to an aqueous alkali metal oxide or hydroxide solution, aqueous ammonia, or aqueous carbamide solution which functions as a precipitator to coprecipitate;

2) after step 1), providing a crude catalyst by washing, drying in the air, calcining, and reducing in hydrogen gas; and 3) using an aqueous alkali metal hydroxide solution to remove any alumina in the crude catalyst obtained in steps 1), and 2) to provide a composite metal oxides catalyst $CuO$—$NiO$—$Fe_3O_4$, $NiO$—$Fe_3O_4$, $CuO$—$Fe_3O_4$, or $CuO$—$NiO$.

2. The method of claim 1, wherein the molar ratio of Cu to Ni is from 10:1 to 1:10, and the molar ratio of Cu to Fe is from 10:1 to 1:10 in $CuO$—$NiO$—$Fe_3O_4$.

3. The method of claim 1, wherein the molar ratio of Ni to Fe in $NiO$—$Fe_3O_4$ is from 10:1 to 1:10.

4. The method of claim 1, wherein the molar ratio of Cu to Fe in $CuO$—$Fe_3O_4$ is from 10:1 to 1:10.

5. The method of claim 1, wherein the molar ratio of Cu to Ni in $CuO$—$NiO$ is from 10:1 to 1:10.

6. The method of claim 1, wherein the mass ratio between the composite metal oxide catalyst and the amine is from 0.01:1 to 1.2:1.

7. The method of claim 1, wherein step 1) comprises coprecipitation conducted at room temperature, and wherein, in step 2), the drying temperature of the catalyst is 50-180° C., the calcining temperature is 300-800° C., and the reducing temperature is 300-800° C.

8. The method of claim 1 wherein the reacting comprise reacting at a reaction temperature of 80-180° C. for 6-36 hours.

* * * * *